(12) United States Patent
Koppel et al.

(10) Patent No.: US 10,376,154 B2
(45) Date of Patent: Aug. 13, 2019

(54) DETECTION OF AORTIC COARCTATION USING PHOTOPLETHYSMOGRAPHY

(71) Applicants: The Feinstein Institute For Medical Research, Manhasset, NY (US); Jerusalem College of Technology, Jerusalem (IL)

(72) Inventors: Robert Koppel, West Hempstead, NY (US); Meir Nitzan, Bet El (IL)

(73) Assignees: The Feinstein Institute for Medical Research, Manhasset, NY (US); Jerusalem College of Technology, Jerusalem (IL)

(*) Notice: Subject to any disclaimer, the term of this patent is extended or adjusted under 35 U.S.C. 154(b) by 269 days.

(21) Appl. No.: 15/125,203

(22) PCT Filed: Mar. 12, 2015

(86) PCT No.: PCT/US2015/020077
§ 371 (c)(1),
(2) Date: Sep. 12, 2016

(87) PCT Pub. No.: WO2015/142603
PCT Pub. Date: Sep. 24, 2015

(65) Prior Publication Data
US 2017/0164842 A1    Jun. 15, 2017

Related U.S. Application Data

(60) Provisional application No. 61/954,700, filed on Mar. 18, 2014.

(51) Int. Cl.
*A61B 5/00* (2006.01)
*A61B 5/02* (2006.01)
(Continued)

(52) U.S. Cl.
CPC ........ *A61B 5/02007* (2013.01); *A61B 5/0261* (2013.01); *A61B 5/0295* (2013.01);
(Continued)

(58) Field of Classification Search
CPC ............ A61B 5/02007; A61B 5/02427; A61B 5/0261; A61B 5/0295; A61B 5/6825;
(Continued)

(56) References Cited

U.S. PATENT DOCUMENTS 6,334,065 B1    12/2001   Al-Ali et al.
6,616,613 B1    9/2003    Goodman
(Continued)

OTHER PUBLICATIONS

PCT International Search Report and Written Opinion dated Jun. 3, 2015 for PCT International Patent Application No. PCT/US2015/20077, 9 pages.
(Continued)

*Primary Examiner* — Paula J Stice
(74) *Attorney, Agent, or Firm* — Amster, Rothstein & Ebenstein LLP (57) ABSTRACT

Methods and systems are described for detecting the likelihood of an aortic coarctation in an infant using photoplethysmographic pulse signals obtained from the hand and foot of the infant.

23 Claims, 5 Drawing Sheets

(51) Int. Cl.
  *A61B 5/026* (2006.01)
  *A61B 5/1455* (2006.01)
  *A61B 5/024* (2006.01)
  *A61B 5/0295* (2006.01)
  *G16H 50/30* (2018.01)

(52) U.S. Cl.
  CPC ...... *A61B 5/02427* (2013.01); *A61B 5/14551* (2013.01); *A61B 5/6825* (2013.01); *A61B 5/6829* (2013.01); *A61B 5/725* (2013.01); *A61B 5/7207* (2013.01); *A61B 5/7246* (2013.01); *A61B 5/7275* (2013.01); *A61B 5/7203* (2013.01); *A61B 2503/04* (2013.01); *A61B 2503/045* (2013.01); *G16H 50/30* (2018.01)

(58) Field of Classification Search
  CPC ... A61B 5/6829; A61B 5/6826; A61B 5/7275; G06F 19/00
  See application file for complete search history.

(56) References Cited

U.S. PATENT DOCUMENTS

| | | | |
|---|---|---|---|
| 6,714,804 B2 | 3/2004 | Al-Ali et al. | |
| 6,898,452 B2 | 5/2005 | Al-Ali et al. | |
| 6,909,912 B2 | 6/2005 | Melker | |
| 7,024,235 B2 | 4/2006 | Melker et al. | |
| 7,127,278 B2 | 10/2006 | Al-Ali et al. | |
| 7,761,728 B2 | 7/2010 | Al-Ali et al. | |
| 7,891,355 B2 | 2/2011 | Al-Ali et al. | |
| 7,894,868 B2 | 2/2011 | Al Ali et al. | |
| 7,899,507 B2 | 3/2011 | Al Ali et al. | |
| 8,255,028 B2 | 8/2012 | Al Ali et al. | |
| 8,364,223 B2 | 1/2013 | Al Ali et al. | |
| 2004/0254485 A1 | 12/2004 | Wu et al. | |
| 2008/0009754 A1 | 1/2008 | Chang | |
| 2008/0119741 A1 | 5/2008 | Friedman et al. | |
| 2010/0191080 A1 | 7/2010 | Mills | |
| 2012/0078069 A1 | 3/2012 | Melker | |
| 2013/0310700 A1 | 11/2013 | Wiard et al. | |
| 2013/0331670 A1 | 12/2013 | Kiani | |
| 2015/0366469 A1* | 12/2015 | Harris | A61B 5/0245 600/301 |

OTHER PUBLICATIONS

Nitzan M et al., entitled "The difference in pulse transit time to the toe and finger measured by photoplethysmography," Physiol Meas. Feb. 2002;23(1):85-93. Abstract only.

Kwang-Suk S et al., entitled "Estimation of Continuous Blood Pressure with Amplitude of Photoplethymogram and Pulse Transit Time of Finer and Toe," Korean J Anesthesiol, Aug. 2007;53(2):159-168. Abstract.

Ailes E C et al., entitled "Estimated Number of Infants Detected and Missed by Britical Congenital Heart Defect Screening," Pediatrics, vol. 135, No. 6, Jun. 2015, 1000-1008.

Lannering K et al., entitled "Late Diagnosis of Coarctation Despite Prenatal Ultrasound and Postnatal Pulse Oximetry," Pediatrics, vol. 136, No. 2, Aug. 2015, e406-e412.

Nitzan M et al., entitled "Pulse oximetry: fundamentals and technology update," Medical Devices: Evidence and Research 2014:7, 231-239.

* cited by examiner

DETECTION OF AORTIC COARCTATION USING PHOTOPLETHYSMOGRAPHY

CROSS-REFERENCE TO RELATED APPLICATIONS

This application is a U.S. national stage entry under 35 U.S.C. 071 of PCT International Patent Application No. PCT/US2015/020077, filed Mar. 12, 2015, which claims the benefit of U.S. Provisional Patent Application No. 61/954,700, filed Mar. 18, 2014, the contents of which are incorporated herein by reference into the subject application.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

Congenital Heart Disease (CHD) occurs in approximately 9/1,000 live births and 25% of those have critical congenital heart disease (CCHD), defined as requiring surgery or catheter intervention in the first year of life (Mahle, 2009). CCHD can lead to severe complications, including cardiovascular collapse, neurologic injury, and even death if not detected in a timely fashion. Newborn infants with CCHD may have hypoxemia that is not clinically apparent prior to hospital discharge, and not all cases are detected by physical examination (Richmond, 2001).

Pulse oximetry is an objective, non-invasive test that quantifies the percent of hemoglobin that is saturated with oxygen and is widely used as a screening tool for early detection of CCHD (Koppel, 2003; Mahle, 2009; Thangaratinam, 2012). Pulse oximetry screening of all newborns for CCHD has been endorsed by many organizations including the American Academy of Pediatrics (AAP), American College of Cardiology, and American Heart Association (Kemper, 2011; Mahle, 2012). However, the screening as it is currently performed has low sensitivity for coarctation of the aorta (CoA) (Mahle, 2009; Prudhoe, 2013). Coarctation is one of the most common CCHD overall with an incidence of 4/10,000 (Reller, 2008), and the diagnosis of CoA by physical examination is often delayed (Punukollu, 2011).

In patients with CoA, blood flow through the constricted region of the aorta is reduced and the arterial blood pressure and pulse pressure in the upper body are higher than those in the lower body (Beekman, 2001; Goldman, 1949). Previous studies have recommended measurement of upper and lower limb blood pressures to improve the clinical diagnosis of CoA (Beekman, 2001; Brierley, 2002). However, the variation in blood pressures of healthy newborns' extremities is too wide for this method to reliably assess for CoA (Crossland, 2004).

Coarctation may be detected by differential cyanosis on pulse oximetry screening if the test is performed at a point in time when the ductus arteriosus is patent, thereby allowing blood to flow from the right ventricle to the descending aorta. However, in approximately half of all cases of CoA, oximetry demonstrates "normal" saturation, likely because screening is performed after the ductus arteriosus has closed (de Wahl-Granelli, 2007; Mahle, 2009). Despite this "normal" arterial oxygen saturation, the reduction in aortic blood flow causes ischemia to develop in the lower half of the body (Ward, 1990). As a result, the risk of morbidity and mortality rapidly increases in cases of delayed diagnosis of CoA (Punukollu, 2011).

A thorough physical examination includes simultaneous palpation of the radial and femoral pulses. This technique is important for determining the relative pulse volume and whether there is a delay in pulse transmission (MacLeod, 2009). Normally, the radial and femoral pulse upstrokes occur simultaneously. Delayed arrival of the femoral pulse, often associated with diminished amplitude, is indicative of CoA. However, this physical examination technique is challenging to perform in the neonatal population, and a reliable alternative method has not yet been developed. Moreover, the development of these findings commonly occurs after 48 hours of life at a time when many infants have already been discharged home from the hospital (Ward, 1990).

Photoplethysmography (PPG) is the measurement of the systolic increase in tissue blood volume by light transmission through an extremity. The systolic increase in the arterial blood pressure is accompanied by an increase in arterial blood volume resulting in reduced light transmission. PPG wavelengths in the red and infrared regions also serve as the basis for pulse oximetry (Sinha, 2013).

The present invention addresses the need for improved methods and apparatus for detecting aortic coarctation in newborns using photoplethysmographic measurements.

SUMMARY OF THE INVENTION

The present invention provides methods for detecting the likelihood of an aortic coarctation in an infant comprising: a) obtaining photoplethysmographic (PPG) signals from the right hand and from a foot of the infant; b) identifying end-diastolic maxima and minima of systolic decrease for the hand PPG pulses and for the foot PPG pulses, and using the maxima and minima to determine one or both of the following: b1) time delay (TD) between the end-diastolic maxima for the hand PPG pulses and the end-diastolic maxima for the foot PPG pulses (f-hTD), and/or b2) PPG pulse amplitude (AM) between the end-diastolic maxima and minima for the hand PPG pulses and for the foot PPG pulses; c) if PPG pulse amplitude (AM) is determined, determining a relative pulse amplitude (rAM) by dividing the AM by the end-diastolic minima to obtain a rAM for the foot (rAM-F) PPG pulses and a rAM for the hand (rAM-H) PPG pulses; d) calculating mean and standard deviation (SD) of f-hTD, and/or rAM for the foot (rAM-F) and rAM for the hand (rAM-H) for the PPG pulses in the selected section, and discarding values deviating from the mean by 2 standard deviations or more from the calculation of the mean; e) if mean foot rAM-F and mean hand rAM-H are calculated, determining a ratio F/H between mean foot rAM-F and mean hand rAM-H, and/or determining a ratio H/F between mean hand rAM-H and mean foot rAM-F; and optionally, obtaining a multiplication product of H/F times f-hTD and/or a multiplication product of F/H times f-hTD; and f) detecting the likelihood of an aortic coarctation in the infant if one or more of: the f-hTD is elevated above normal, or the ratio F/H is decreased below normal, or the ratio H/F is increased above normal, or the product H/F times f-hTD is increased above normal.

The invention also provides systems for detecting the likelihood of an aortic coarctation in an infant comprising a photoplethysmograph of at least two channels, one or more computing devices comprising one or more processors, a memory unit, a display device, and a computer-readable storage medium including computer-readable code that is read by the one or more processors to perform a method comprising the steps of: a) accessing photoplethysmographic (PPG) signals from the right hand and from a foot of the infant; b) identifying end-diastolic maxima and minima of systolic decrease for the hand PPG pulses and for the foot PPG pulses, and using the maxima and minima to determine one or both of the following: b1) time delay (TD) between the end-diastolic maxima for the hand PPG pulses and the end-diastolic maxima for the foot PPG pulses (f-hTD), and/or b2) PPG pulse amplitude (AM) between the end-diastolic maxima and minima for the hand PPG pulses and for the foot PPG pulses; c) if PPG pulse amplitude (AM) is determined, determining a relative pulse amplitude (rAM) by dividing the AM by the end-diastolic minima to obtain a rAM for the foot (rAM-F) PPG pulses and a rAM for the hand (rAM-H) PPG pulses; d) calculating mean and standard deviation (SD) of f-hTD, and/or rAM for the foot (rAM-F) and rAM for the hand (rAM-H) for the PPG pulses in the selected section, and discarding values deviating from the mean by 2 standard deviations or more from the calculation of the mean; e) if mean foot rAM-F and mean hand rAM-H are calculated, determining a ratio F/H between mean foot rAM-F and mean hand rAM-H, and/or determining a ratio H/F between mean hand rAM-H and mean foot rAM-F; and optionally, obtaining a multiplication product of H/F times f-hTD and/or a multiplication product of F/H times f-hTD; and f) outputting to the display device one or more of f-hTD, ratio F/H, ratio H/F, f-hTD and ratio F/H, the product H/F times f-hTD, and the product F/H times f-hTD.

DETAILED DESCRIPTION OF THE INVENTION

The present invention provides a method for detecting the likelihood of an aortic coarctation in an infant comprising:
a) obtaining photoplethysmographic (PPG) signals from the right hand and from a foot of the infant;
b) identifying end-diastolic maxima and minima of systolic decrease for the hand PPG pulses and for the foot PPG pulses, and using the maxima and minima to determine one or both of the following:
b1) time delay (TD) between the end-diastolic maxima for the hand PPG pulses and the end-diastolic maxima for the foot PPG pulses (f-hTD), and/or b2) PPG pulse amplitude (AM) between the end-diastolic maxima and minima for the hand PPG pulses and for the foot PPG pulses;
c) if PPG pulse amplitude (AM) is determined, determining a relative pulse amplitude (rAM) by dividing the AM by the end-diastolic minima to obtain a rAM for the foot (rAM-F) PPG pulses and a rAM for the hand (rAM-H) PPG pulses;
d) calculating mean and standard deviation (SD) of f-hTD, and/or rAM for the foot (rAM-F) and rAM for the hand (rAM-H) for the PPG pulses in the selected section, and discarding values deviating from the mean by 2 standard deviations or more from the calculation of the mean;
e) if mean foot rAM-F and mean hand rAM-H are calculated, determining a ratio F/H between mean foot rAM-F and mean hand rAM-H, and/or determining a ratio H/F between mean hand rAM-H and mean foot rAM-F; and optionally, obtaining a multiplication product of H/F times f-hTD and/or a multiplication product of F/H times f-hTD; and
f) detecting the likelihood of an aortic coarctation in the infant if one or more of:
the f-hTD is elevated above normal, or
the ratio F/H is decreased below normal, or
the ratio H/F is increased above normal, or
the product H/F times f-hTD is increased above normal.

The method can further comprise one or more steps of low-pass filtering PPG signals to reduce high frequency noise, selecting a section of PPG pulses without movement noise for analysis, and smoothing hand PPG signal and smoothing foot PPG signal using a moving average filter.

The present invention further provides a method for detecting the likelihood of an aortic coarctation in an infant comprising:
a) obtaining photoplethysmographic (PPG) signals from the right hand and from a foot of the infant;
b) low-pass filtering PPG signals to reduce high frequency noise;
c) selecting a section of PPG pulses without movement noise for further analysis;
d) smoothing hand PPG signal and smoothing foot PPG signal using a moving average filter;
e) identifying end-diastolic maxima and minima of systolic decrease for the hand PPG pulses and for the foot PPG pulses;
f) using the maxima and minima identified in e) to determine one or both of the following:
f1) time delay (TD) between the end-diastolic maxima for the hand PPG pulses and the end-diastolic maxima for the foot PPG pulses (f-hTD), and/or
f2) PPG pulse amplitude (AM) between the end-diastolic maxima and minima for the hand PPG pulses and for the foot PPG pulses;
g) if PPG pulse amplitude (AM) is determined, determining a relative pulse amplitude (rAM) by dividing the AM by the end-diastolic minima to obtain a rAM for the foot (rAM-F) PPG pulses and a rAM for the hand (rAM-H) PPG pulses;
h) calculating mean and standard deviation (SD) of f-hTD, and/or rAM for the foot (rAM-F) and rAM for the hand (rAM-H) for the PPG pulses in the selected section, and discarding values deviating from the mean by 2 standard deviations or more from the calculation of the mean;
i) if mean foot rAM-F and mean hand rAM-H are calculated, determining a ratio F/H between mean foot rAM-F and mean hand rAM-H, and/or determining a ratio H/F between mean hand rAM-H and mean foot rAM-F; and optionally, obtaining a multiplication product of H/F times f-hTD and/or a multiplication product of F/H times f-hTD; and j) detecting the likelihood of an aortic coarctation in the infant if one or more of:
the f-hTD is elevated above normal, or
the ratio F/H is decreased below normal, or
the ratio H/F is increased above normal, or
the product H/F times f-hTD is increased above normal.

The invention also provides a system for detecting the likelihood of an aortic coarctation in an infant comprising a photoplethysmograph of at least two channels, one or more computing devices comprising one or more processors, a memory unit, a display device, and a computer-readable storage medium including computer-readable code that is read by the one or more processors to perform a method comprising the steps of:

a) accessing photoplethysmographic (PPG) signals from the right hand and from a foot of the infant;

b) identifying end-diastolic maxima and minima of systolic decrease for the hand PPG pulses and for the foot PPG pulses, and using the maxima and minima to determine one or both of the following:

b1) time delay (TD) between the end-diastolic maxima for the hand PPG pulses and the end-diastolic maxima for the foot PPG pulses (f-hTD), and/or b2) PPG pulse amplitude (AM) between the end-diastolic maxima and minima for the hand PPG pulses and for the foot PPG pulses;

c) if PPG pulse amplitude (AM) is determined, determining a relative pulse amplitude (rAM) by dividing the AM by the end-diastolic minima to obtain a rAM for the foot (rAM-F) PPG pulses and a rAM for the hand (rAM-H) PPG pulses;

d) calculating mean and standard deviation (SD) of f-hTD, and/or rAM for the foot (rAM-F) and rAM for the hand (rAM-H) for the PPG pulses in the selected section, and discarding values deviating from the mean by 2 standard deviations or more from the calculation of the mean;

e) if mean foot rAM-F and mean hand rAM-H are calculated, determining a ratio F/H between mean foot rAM-F and mean hand rAM-H, and/or determining a ratio H/F between mean hand rAM-H and mean foot rAM-F; and optionally, obtaining a multiplication product of H/F times f-hTD and/or a multiplication product of F/H times f-hTD; and f) outputting to the display device one or more of f-hTD, ratio F/H, ratio H/F, f-hTD and ratio F/H, the product H/F times f-hTD, and the product F/H times f-hTD.

The system can further comprise performing one or more steps of low-pass filtering PPG signals to reduce high frequency noise, selecting a section of PPG pulses without movement noise for analysis, and smoothing hand PPG signal and smoothing foot PPG signal using a moving average filter.

The invention further provides a system for detecting the likelihood of an aortic coarctation in an infant comprising a photoplethysmograph of at least two channels, one or more computing devices comprising one or more processors, a memory unit, a display device, and a computer-readable storage medium including computer-readable code that is read by the one or more processors to perform a method comprising the steps of:

a) accessing photoplethysmographic (PPG) signals from the right hand and from a foot of the infant;

b) low-pass filtering PPG signals to reduce high frequency noise;

c) selecting a section of PPG pulses without movement noise for further analysis;

d) smoothing hand PPG signal and smoothing foot PPG signal using a moving average filter;

e) identifying end-diastolic maxima and minima of systolic decrease for the hand PPG pulses and for the foot PPG pulses;

f) using the maxima and minima identified in e) to determine one or both of the following:

f1) time delay (TD) between the end-diastolic maxima for the hand PPG pulses and the end-diastolic maxima for the foot PPG pulses (f-hTD), and/or f2) PPG pulse amplitude (AM) between the end-diastolic maxima and minima for the hand PPG pulses and for the foot PPG pulses;

g) if PPG pulse amplitude (AM) is determined, determining a relative pulse amplitude (rAM) by dividing the AM by the end-diastolic minima to obtain a rAM for the foot (rAM-F) PPG pulses and a rAM for the hand (rAM-H) PPG pulses;

h) calculating mean and standard deviation (SD) of f-hTD, and/or rAM for the foot (rAM-F) and rAM for the hand (rAM-H) for the PPG pulses in the selected section, and discarding values deviating from the mean by 2 standard deviations or more from the calculation of the mean;

i) if mean foot rAM-F and mean hand rAM-H are calculated, determining a ratio F/H between mean foot rAM-F and mean hand rAM-H, and/or determining a ratio H/F between mean hand rAM-H and mean foot rAM-F; and optionally, obtaining a multiplication product of H/F times f-hTD and/or a multiplication product of F/H times f-hTD; and j) outputting to the display device one or more of f-hTD, ratio F/H, ratio H/F, f-hTD and ratio F/H, the product H/F times f-hTD, and the product F/H times f-hTD.

Preferably, the photoplethysmograph has an infrared light source.

PPG pulses can be obtained from the right foot of the infant or from the left foot of the infant.

PPG pulses can be low-pass filtered, for example, at 0-40 Hz.

In different embodiments, the likelihood of an aortic coarctation can be determined, for example, using f-hTD, or using ratio F/H, or using f-hTD and ratio F/H, or using the product H/F times f-hTD.

f-hTD values for normal infants have a range of 15-50 milliseconds (ms) and a mean of 35 ms. In one embodiment, a f-hTD value equal to or higher than a predetermined value in a range of 50-60 ms can be used as indicative that the infant has aortic coarctation. For example, a f-hTD value of 50 ms of more, or of 55 ms of more, or of 60 ms of more can be used as indicative that the infant has aortic coarctation.

Normal infants have a mean ratio F/H of 0.9. In one embodiment, a ratio F/H equal to or less than a predetermined value in a range of 0.4-0.6 can be used as indicative that the infant has aortic coarctation. For example, a ratio F/H of 0.6 or less, or of 0.5 or less, or of 0.4 or less can be used as indicative that the infant has aortic coarctation.

In one embodiment, a f-hTD value equal to or higher than a predetermined value in a range of 50-60 ms and a ratio F/H equal to or less than a predetermined value in a range of 0.4-0.6 can be used as indicative that the infant has aortic coarctation.

Normal infants have a mean product of ratio H/F times f-hTD of 45. In one embodiment, a product of ratio H/F times f-hTD equal to or higher than a predetermined value in a range of 80-100 can be used as indicative that the infant has aortic coarctation. For example, a product of ratio H/F times f-hTD of 80 or more, or of 90 or more, or of 100 or more can be used as indicative that the infant has aortic coarctation.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

This invention provides quantitative methods to determine the time delay of the pulse arrival at the foot relative to the hand to improve the ability of clinicians to detect CoA. In 1949, Goldman and Schroeder performed simultaneous proximal and distal PPG measurements in patients with CoA and showed significantly diminished pulse amplitude in the toe relative to the finger. PPG pulses in the toe were also found to be delayed relative to those in the finger (Goldman, 1949). The observed PPG changes were not quantified or statistically analyzed.

The present inventors hypothesized that analysis of the photoplethysmographic waveforms from clinical pulse oximeter probes and a PPG device would enhance the ability to detect aortic obstruction in newborns with CoA during routine screening. In the present study, hand and foot PPG pulse wave recordings were obtained from 31 healthy newborns and 8 infants with CoA, and differences in pulse amplitudes and foot-hand pulse transit time were analyzed.

Methods

Subjects

The study was approved by the Institutional Review Board. Parental written informed consent was obtained prior to participant enrollment. Well-appearing newborns were evaluated prior to hospital discharge to establish normative data for the foot-hand pulse transit time difference. The risk of occult CCHD in this patient group was anticipated to be very low based on the absence of clinical signs of CCHD and having passed oximetry screening. Study subjects were either (a) healthy-appearing newborns at greater than 24 hours of age screened prior to discharge home, or (b) infants with echocardiographic diagnosis of CoA or aortic narrowing. The evaluation time point of greater than 24 hours and prior to discharge was selected so that the investigation would be consistent with the AAP Policy Statement on pulse oximetry screening (Mahle, 2012). Data collected on each infant included the following: date and time of birth; birthweight (grams); blood pressures, pre- and post-ductal saturation of peripheral oxygen ($SpO_2$); and echocardiography findings for infants with CoA.

Other than two infants with fetal echocardiographic suspicion of CoA, the remaining six infants in the series became symptomatic after discharge from the hospital (mean age at presentation=23 days). One infant with CoA presented to the hospital emergency department in extremis. Stabilization of this infant included prostaglandin infusion to re-open the ductus arteriosus, dopamine and milrinone, as well as multiple transfusions of packed red blood cells and fresh frozen plasma. Another infant in the study had re-coarctation as a complication following repair of an interrupted aortic arch. This infant presented with a significant upper-lower extremity blood pressure gradient and had an anastamotic stricture on echocardiogram. Of the two cases with fetal ECHO suspicion of CoA, one infant did not have evidence of CoA on serial postnatal echocardiograms and was discharged home only to be readmitted four days later in respiratory distress secondary to critical CoA.

For each healthy infant enrolled, pulse oximeter probes were already in place on the right hand and foot for simultaneous measurement of pre- and post-ductal oxygen saturation as recommended in national guidelines for CCHD screening (Kemper, 2011). After recording the saturation results, the two probes were disconnected from the pulse oximeters and attached to the PPG device—designed and built at the Jerusalem College of Technology (JCT). For infants with echocardiographic diagnosis of CoA, pulse oximeter probes were already in place on the right hand and foot for simultaneous monitoring of pre- and post-ductal $SpO_2$ as is customary in the management of infants with this condition. The two probes were briefly disconnected from the pulse oximeters and attached instead to the JCT PPG device. An additional probe was attached to the opposite foot to enable continuous $SpO_2$ monitoring. For infants in both groups, the PPG device acquired signals for approximately 5 minutes and each recording was repeated to assess reproducibility of results. The PPG signals were saved to a hospital-registered, password-protected laptop computer connected to the PPG device.

The PPG Device

Figure 1A:
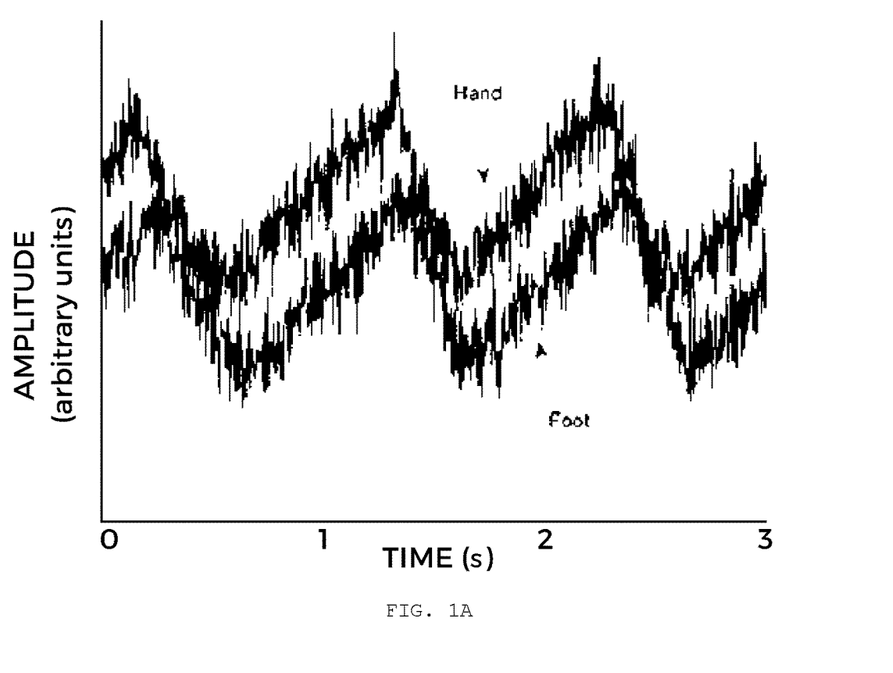
FIG. 1A. Raw, unsmoothed photoplethysmography (PPG) curves from an infant with coarctation. PPG signals have been inverted in the figure.

Neonatal pulse oximeter probes (Nellcor Neonatal $SpO_2$ sensor, Covidien, Mansfield, Mass., USA) were applied to the right hand and foot. PPG signals were obtained using only the infrared light source in the oximeter probes, and the photodetector signals were directed to the PPG device. The PPG signals were low-pass filtered (0-40 Hz) to reduce high frequency noise, and after amplification they were sampled at a rate of 1,000 samples per second with 16-bit resolution and stored for further processing and analysis. A representative example of the hand and foot PPG signals before signal processing is shown in FIG. 1a. Light transmission through the hand and foot decreases during systole due to the increase in tissue blood volume; consequently, the maxima of the PPG signals occur at end-diastole.

Signal Analysis

Figure 1B:
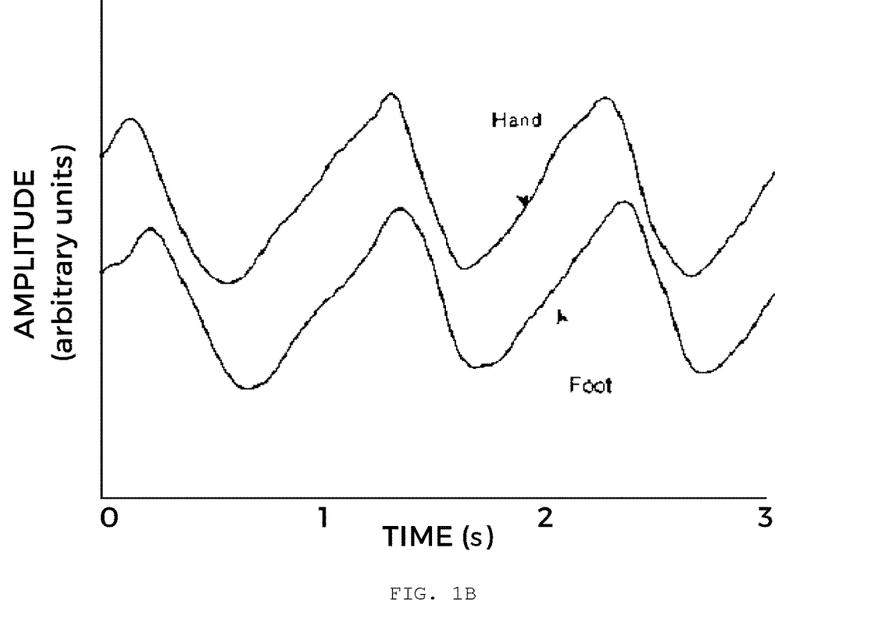
FIG. 1B. PPG curves from FIG. 1A after smoothing.
Figure 2:
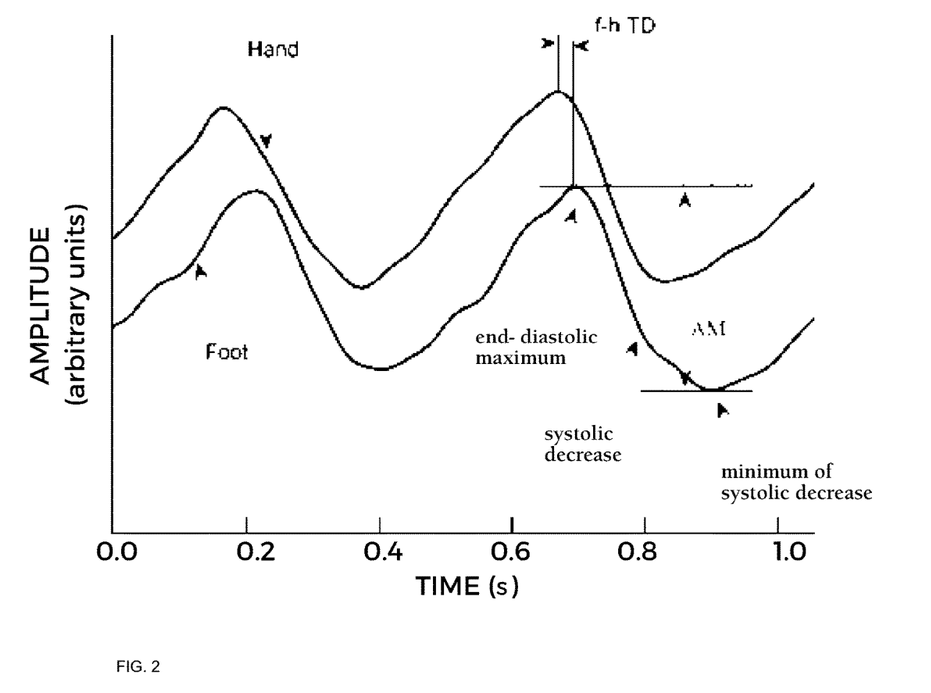
FIG. 2. Two pulses from PPG curves depicting end-diastolic maximum, systolic decrease, minimum of systolic decrease, PPG pulse amplitude (AM), and foot-hand time delay (f-hTD). PPG signals have been inverted in the figure.

In each PPG recording two regions of 10-20 PPG signals without motion artifact were selected. The hand and foot PPG signals were averaged with a 21 sample moving average filter performed twice, serially. FIG. 1b depicts the waves of FIG. 1a after this smoothing process. The end-diastolic maxima and minima of systolic decrease were then algorithmically-identified and used to determine the following: time delay for the start of the systolic decrease between the foot and hand PPG pulses (f-hTD); and PPG pulse amplitude (AM), as illustrated in FIG. 2. The relative value of the latter (rAM) was defined as AM divided by the minimum of the PPG curve (the minimum of the systolic decrease); this value is proportional to the tissue blood volume increase in the foot or hand, respectively, during systole (Nitzan, 1998, 2009). For each infant, the mean and standard deviation (SD) of f-hTD and rAM for the foot (rAM-F) and hand (rAM-H) were calculated for the 10-20 pulses; values that deviated from the mean by 2SD or more (0-3 pulses for each parameter) were discarded. The mean values of f-hTD and rAM for each of the two regions in each recording were taken as the parameter values. Statistical calculations using the Mann-Whitney and Signed Rank tests compared TD, rAM-H, rAM-F, and their ratio (F/H) between the infant groups.

Reproducibility

The reproducibility of f-hTD and rAM values were assessed by performing serial PPG signal recordings on healthy neonates using the same technique with pulse oximeter probes reapplied 1-2 mm from the original sites.

Results

Studies were carried out on 31 healthy infants and 9 infants with CoA. All infants in both groups had normal results on routine pre-discharge pulse oximetry screening (pre- and post-ductal $SpO_2$=97-100%). The range of f-hTD values for the normal infants was 15.5-49.5 milliseconds (ms) (mean±SD: 34.98±8.38 ms) and for the CoA patients was 46.40-132.20 ms (71.80±27.47 ms). This difference is statistically significant, p=0.00003 (Mann-Whitney test), as shown in Table 1. Data from the one infant who presented in extremis were analyzed separately due to his extreme clinical condition. The values of the foot-hand time delay (f-hTD: 38.5 ms) and ratio of the relative value of the PPG pulse amplitude for the foot and hand (F/H: 1.80) for this critical patient were very different than those for the other CoA patients. The low values of f-hTD and rAM-H (and, consequently, the high value of F/H) for this patient can be attributed to his very large PDA and altered hemodynamics secondary to cardiogenic shock resulting from a severe long segment CoA with tubular hypoplasia of the transverse aorta, functionally bicuspid aortic valve, and large apical muscular ventricular septal defect.

Figure 3:
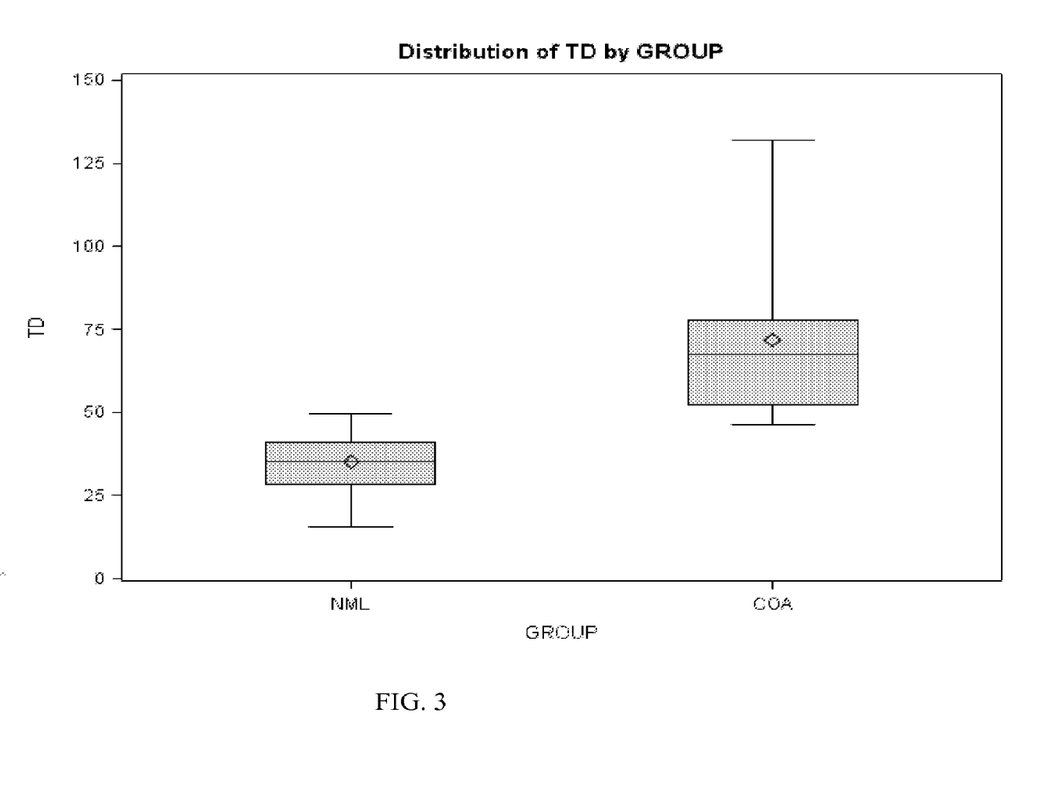
FIG. 3. Scatterplot (left) and boxplot (right) of foot-hand time delay (TD) in ms for normal and CoA neonates.
Figure 4:
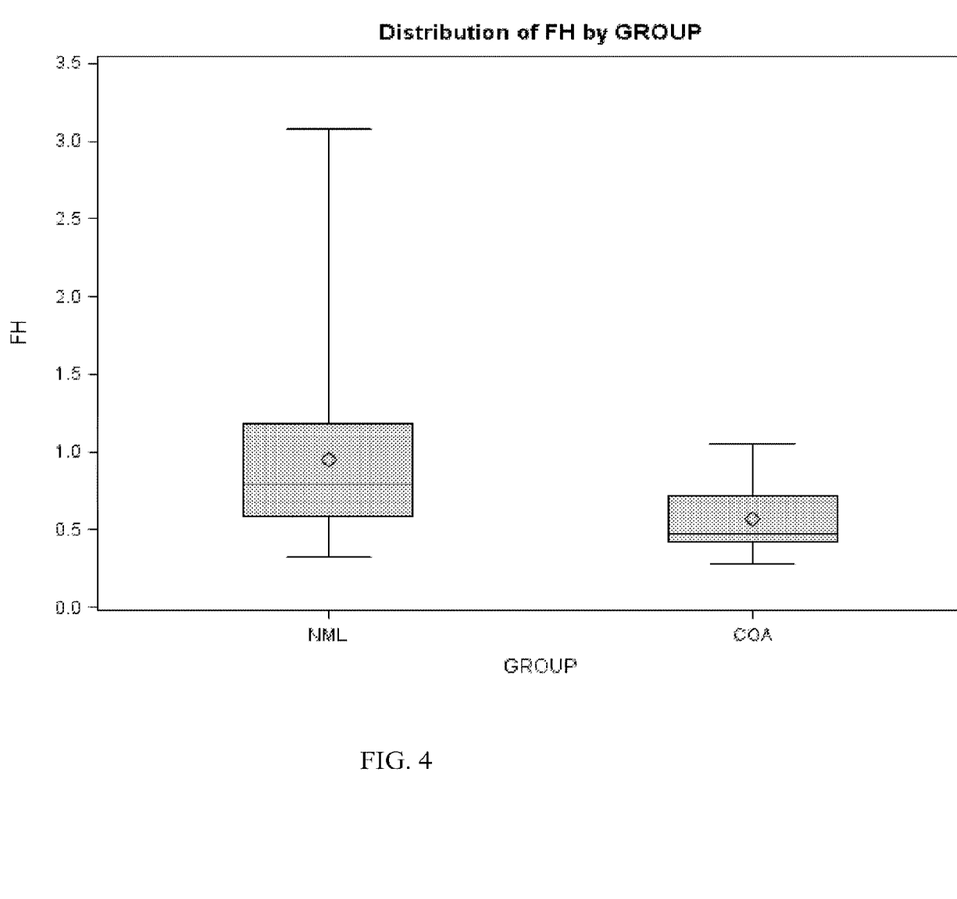
FIG. 4. Scatterplot (left) and boxplot (right) of foot/hand PPG pulse amplitude ratio (F/H) for normal and CoA neonates.
Figure 5:
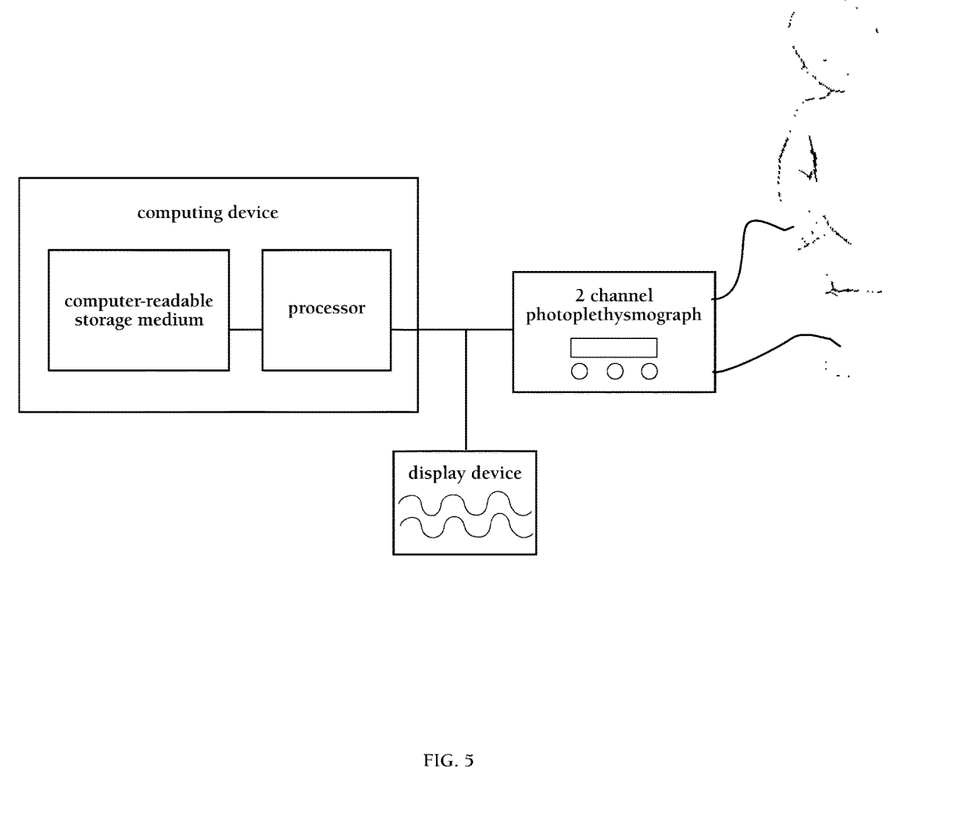
FIG. 5. Schematic of a system for detecting an aortic coarctation in an infant comprising a photoplethysmograph of two channels, a computing device comprising a processor operably connected to the photoplethysmograph and a computer-readable storage medium operably connected to the processor, and a display device operably connected to the photoplethysmograph and to the processor.

The means and standard deviations of rAM-H, rAM-F, and F/H for normal newborns and CoA infants are presented in Table 1. The mean values for rAM did not differ significantly between the hand and foot. The mean value of F/H was significantly lower for CoA patients (0.57±0.25) than for normal infants (0.95±0.53). This difference between groups is statistically significant, p=0.01640 (Mann-Whitney test). Table 2 shows individual means for patients with CoA for f-hTD, rAM-F, rAM-H, and F/H, as well as their clinically relevant anatomical findings on ECHO. The distributions of f-hTD for normal and CoA infants are depicted as a scatterplot and boxplot in FIG. 3, and the distributions of ratio F/H for normal and CoA infants are depicted as a scatterplot and boxplot in FIG. 4.

Calculations were also obtained for the multiplication product of the ratio of H/F times f-hTD. This index resulted in excellent separation of values for normal newborns compared to CoA infants. Mean±SD values for normal infants were 44.63±22.26, while the values for CoA infants were 143.16±73.26 (p-value=0.00004, Mann-Whitney test).

Data were obtained for 6 of the CoA infants both before and after surgical repair. Following surgical repair, the f-hTD decreased and F/H increased toward the values observed in normal newborns. However, the differences between the pre- and post-operative values for f-hTD (71.80±27.47 versus 51.38±18.17), rAM-H (1.62±1.07 versus 1.85±1.08), rAM-F (0.87±0.48 versus 1.39±1.19), and F/H (0.57±0.25 versus 0.74±0.39) were not of statistical significance (Signed Rank test).

Discussion

The present results demonstrate that compared to a population of healthy infants, newborns with CoA have a measurable prolongation of the time delay and diminished pulse amplitude in the foot relative to the right hand. The physiologic basis for this observation is that pulse wave velocity (PWV), which is generally measured at end-diastole just as the systolic upstroke is starting, increases with higher diastolic blood pressures (Nurnberger, 2003). The low blood pressure distal to the CoA results in an increase in the blood pressure-pulse transit time to the lower extremity, a finding that is most likely due to the decreased PWV associated with increased arterial distensibility (Johnson, 1950; Lewis, 1933). Blood pressure PWV also increases with more arterial stiffness that can be altered by either structural or functional changes in the arterial wall. Although one does not anticipate structural changes such as alterations in elastin and collagen fibers, functional changes in the arterial wall related to blood pressure and sympathetic activity, may influence the degree of arterial stiffness in newborns.

In the present series, TD and F/H improved after surgical repair of CoA but did not return to values observed in normal infants. This finding is consistent with what is known about the generalized arteriopathy in patients with CoA (Rosenthal, 2005). Although typically considered to be a localized abnormality, CoA should be regarded as a diffuse arteriopathy and part of a spectrum of more diffuse arterial pathophysiology possibly related to a developmental abnormality (Warnes, 2003). Brilli et al. and Pfammatter noted severely abnormal pulsatility of the distal segment prior to surgical repair of CoA that did not normalize post-operatively (1998; 2004). The vascular reactivity and mechanical properties of large arteries may be impaired despite successful early CoA repair (De Devitiis, 2001). Vogt et al. found impairment of aortic elastic properties in the ascending aorta (rather than the descending aorta), and that these abnormalities persisted into the early post-operative period (2005). Despite early CoA repair by 2-3 months of age, 28% of affected children—including 21% without any residual aortic obstruction—had hypertension at rest or during ambulation (O'Sullivan, 2002). Therefore, CoA should be considered a lifelong disease process with medical consequences that persist despite surgical repair.

Despite improvements in clinical medicine, fetal echocardiography, and pulse oximetry screening, timely diagnosis of CoA remains a vexing clinical problem for pediatricians (Punukollu, 2011; Ruey-Kang, 2008; Walsh, 2013). Aamir et al. described the experience with delayed diagnosis of CCHD in New Jersey over a period of 5 years (2007). Twenty-eight of the 47 infants with delayed diagnosis in a population of approximately 670,000 had CoA. A similar study analyzing ten years of birth data from the Florida Birth Defect Registry found that the most common CCHD among late-detected infants was CoA (33.3%, N=275/825 in a total birth population of 2,135,000) (Dawson, 2013). These late-detected cases were associated with 52% more hospital admissions, 18% more hospital days, and 35% higher inpatient costs during infancy (Peterson, 2013). Due to the morbidity and mortality resulting from the delayed detection of CoA, several authors have recommended early pediatric follow-up with particular emphasis on examination of the cardiovascular system as well as parental education to observe for clinical signs of CoA (Abu Harb, 1994; Ward, 1990).

Mouledoux and Walsh reported on the diagnostic gap for detection of CCHD prior to introduction of CCHD screening in Tennessee (2013). Their findings confirmed that CoA is the most common CCHD missed by both fetal sonography and physical examination, and raised the concern that CoA is also the lesion most likely to be missed by pulse oximetry. Although very sensitive for lesions that commonly present with hypoxemia, pulse oximetry screening was already recognized in the earliest reports as having limited sensitivity for the detection of CoA (Kao, 1995). This finding has subsequently been confirmed in multiple studies worldwide (Prudhoe, 2013). For all of the aforementioned reasons, CoA was not included in the CCHD 7—the list of primary targets for which oximetry performs well as a screening test (Kemper, 2011). This predicament further emphasizes the importance of improving currently available newborn screening methods.

TABLE 1

|  | f-hTD (ms) | rAM-H (%) | rAM-F (%) | F/H |
|---|---|---|---|---|
| Normal (n = 31) | 34.98 ± 8.38 | 1.18 ± 0.72 | 0.99 ± 0.69 | 0.95 ± 0.53 |
| CoA (n = 9) | 71.80 ± 27.47 | 1.62 ± 1.07 | 0.87 ± 0.48 | 0.57 ± 0.25 |
|  | p = 0.00003 | p = 0.27312 | p = 0.65103 | p = 0.01640 |

TABLE 2

| Patient | Clinical Detection & Age at Presentation | f-hTD (ms) | rAM-H (%) | rAM-F (%) | F/H | Anatomy |
|---|---|---|---|---|---|---|
| A | Blood pressure gradient after repair of interrupted aortic arch; 1-month old | 56.4 | 3.99 | 1.72 | 0.43 | Interrupted aortic arch repair. |
| B | Tachypnea; 5-days old | 46.4 | 0.96 | 0.48 | 0.51 | Moderate long segment coarctation w/ mild tubular hypoplasia of transverse aortic arch. |
| C | Fetal suspicion but no evidence of CoA on initial neonatal echo; re-admitted at 1-week of age with tachypnea | 67.9 | 1.02 | 0.42 | 0.47 | Discrete juxtaductal coarctation of aorta. |
| D | Tachypnea; 41-days old | 67.2 | 2.05 | 0.91 | 0.44 | Long segment coarctation of the aorta distal to L-subclavian artery. Common brachiocephalic trunk giving rise to R-subclavian, R- & L-carotid arteries. |
| E | Respiratory distress; 6-days old | 84.6 | 0.88 | 0.25 | 0.28 | Severe discrete juxtaductal coarctation. L-subclavian artery distally displaced toward coarctation region. Mildly hypoplastic distal transverse aortic arch. Small PDA w/ bidirectional shunt. |
| F | Fetal suspicion of hypoplastic left heart syndrome. | 132.2 | 1.12 | 0.91 | 0.81 | Mildly hypoplastic ascending aorta. Mild to moderately hypoplastic transverse aortic arch. Discrete juxtaductal coarctation. Large, non-restrictive PDA w/ bidirectional shunt. |
| G | Echocardiogram for evaluation of a murmur; 5-days old | 71.4 | 0.96 | 1.01 | 1.05 | Hypoplasia of transverse aortic arch w/ severe juxtaductal coarctation of aorta just distal to L-subclavian artery. Large, non-restrictive PDA w/ bidirectional shunt. Posterior malalignment VSD; large, L→R, non-restrictive systolic interventricular shunt. |
| H | Tachypnea and hypoxemia; 35-days old | 48.3 | 1.96 | 1.23 | 0.63 | Hypoplastic aortic isthmus w/ juxtaductal narrowing. Small PDA w/ bidirectional shunt. Posterior malalignment VSD; large, bidirectional, non-restrictive shunt. |

TABLE 3

|  | f-hTD (ms) | rAM-H (%) | rAM-F (%) | F/H |
|---|---|---|---|---|
| Pre-operative (n = 6) | 71.80 ± 27.47 | 1.62 ± 1.07 | 0.87 ± 0.48 | 0.57 ± 0.25 |
| Post-operative (n = 6) | 51.38 ± 18.17 | 1.85 ± 1.08 | 1.39 ± 1.19 | 0.74 ± 0.39 |
|  | p = 0.156 | p = 0.312 | p = 0.312 | p = 0.688 |

REFERENCES

Aamir, T., Kruse, L., & Ezeakudo, O. (2007). Delayed diagnosis of critical congenital cardiovascular malformations (CCVM) and pulse oximetry screening of newborns. *Acta Paediatrica*, 96 (8): 1146-1149.

Abu-Harb, M., Wyllie, J., Hey, E., Richmond, S., & Wren, C. (1994). Presentation of obstructive left heart malformations in infancy. *Arch Dis Child Fetal Neonatal Ed.*, 71(3): F179-183.

Beekman R. H. (2001). Coarctation of the aorta. In: Allen, H. D., Gutgesell, H. P., Clark, E. B., et al., eds. *Moss and Adams' heart disease in infants, children and adolescents, 6th ed*. Philadelphia: Lippincott Williams and Wilkins: 994-995.

Brierley J., Redington A. N. (2002). Aortic coarctation and interrupted aortic. In: Anderson R H, Baker, E. J., & McCartney, F. J., eds. *Paediatric Cardiology, 2nd ed*. Churchill Livingstone: Edinburgh, 1531.

Brili, S., Dernellis, J., & Aggeli, C., (1998). Aortic elastic properties in patients with repaired coarctation of aorta. *Am J Cardiol*, 82: 1140-1143.

Chang, R. K., Gurvitz, M., & Rodriguez, S. (2008). Missed Diagnosis of Critical Congenital Heart Disease. *Arch Pediatr Adolesc Med*, 162: 969-974.

Crossland, D. S., Furness, J. C., Abu-Harb, M., Sadagopan, S. N., & Wren, C. (2004). Variability of four limb blood pressure in normal neonates. *Arch Dis Child Fetal Neonatal Ed*, 89: F325-327.

Dawson, A. L., Cassell, C. H., Riehle-Colarusso, T., Grosse, S. D., Tanner, J. P., Kirby, R. S., Watkins, S. M., Correia, J. A., & Olney, R. S. (2013). Factors Associated with Late Detection of Critical Congenital Heart Disease in Newborns. *Pediatrics*, 132(3): e604-611.

de Devitiis, M., Pilla, C., & Kattenhorn, M. (2001). Vascular dysfunction after repair of coarctation of the aorta: impact of early surgery. *Circulation*, 104: 1165-71.

de-Wahl Granelli, A., & Östman-Smith, I. (2007). Noninvasive peripheral perfusion index as a possible tool for screening for critical left heart obstruction. *Acta Paediatrica*, 96 (10): 1455-1459.

Douglas, G., Nicol, F., & Robertson, C. (1999). *MacLeod's Clinical Examination*, 12$^{th}$ edition. Elsevier Health Sciences: Philadelphia, 406.

Goldman, M. L., & Schroeder, H. A. (1949). Photo-electric plethysmography and direct arterial blood pressure measurement as an aid in diagnosis. *Am J Med*, 7: 454.

Johnson, C. A. (1950). The speed of the pulse wave in coarctation of the aorta. *J Lab and Clin Med*, 36: 842.

Kao, B. A., Feit, L. R., & Werner, J. C. (1995). Pulse Oximetry as a screen for congenital heart disease in newborns. *Pediatr Res*, 37: 216A.

Kemper, A. R., Mahle, W. T., Martin, G. R., et al. (2011). Strategies for Implementing Screening for Critical Congenital Heart Disease. *Pediatrics*, 128(5): e1259-1267.

Koppel, R. I., Druschel, C. M., Carter, T., et al. (2003). Effectiveness of pulse oximetry screening for congenital heart disease in asymptomatic newborns. *Pediatrics*, 111 (3): 451-455.

Kuhn, L. A., Sapin, S. O., Grishman, A., & Donoso, E. (1956). The use of indirect arterial pulse tracings in the diagnosis of congenital heart disease. I. Coarctation of the aorta. *Pediatrics*, 18: 193-204.

Lewis, T. (1933). Material relating to coarctation of the aorta of the adult type. *Heart*, 16: 205.

Mahle, W. T., Martin, G. R., Beekman III, R. H., et al. (2012). Endorsement of Health and Human Services Recommendation for Pulse Oximetry Screening for Critical Congenital Heart Disease. *Pediatrics*, 129: 190-192.

Mahle, W. T., Newburger, J. W., Matherne, G. P., et al. (2009). Role of pulse oximetry in examining newborns for congenital heart disease: a scientific statement from the American Heart Association and American Academy of Pediatrics. *Circulation*, 120(5): 447-458.

Manfred, V., Kühn, A., Baumgartner, D., Baumgartner, C., Busch, R., Kostolny, M, & Hess, J. (2005). Impaired Elastic Properties of the Ascending Aorta in Newborns Before and Early After Successful Coarctation Repair: Proof of a Systemic Vascular Disease of the Prestenotic Arteries? *Circulation*, 111: 3269-3273.

Mouledoux, J. H., Walsh, W. F. (2013). Evaluating the Diagnostic Gap: Statewide Incidence of Undiagnosed Critical Congenital Heart Disease Before Newborn Screening With Pulse Oximetry. *Pediatr Cardiol*, 34: 1680-1686.

Nitzan, M., Patron, A., Glik, Z., et al. (2009). Automatic noninvasive measurement of systolic blood pressure using photoplethysmography. *BioMedical Engineering OnLine*, 8: 28.

Nürnberger, J., Dammer, S., Opazo Saez, A., Philipp, T., & Schäfers, R. F. (2003). Diastolic blood pressure is an important determinant of augmentation index and pulse wave velocity in young, healthy males. *J Hum Hypertens*, 17: 153-158.

O'Sullivan, J. J., Derrick, G., Darnell, R. (2002). Prevalence of hypertension in children after early repair of coarctation of the aorta: a cohort study using casual and 24-hour blood pressure measurement. *Heart*, 88: 163-166.

Peterson, C., Dawson, A., Grosse, S. D., Riehle-Colarusso, T., Olney, R. S., Tanner, J. P., Kirby, R. S., Correia, J. A., Watkins, S. M., & Cassell, C. H. (2013). Hospitalizations, costs, and mortality among infants with critical congenital heart disease: How important is timely detection? *Birth Defects Research Part A: Clinical and Molecular Teratology*, 97(10): 664-672.

Pfammatter, J-P., Berdat, P., Carrel, T. (2004). Impaired poststenotic aortic pulsatility after hemodynamically ideal coarctation repair in children. *Pediatric Cardiology*, 25: 495-499.

Prudhoe, S., Abu-Harb, M., Richmond, S., & Wren, C. (2013). Neonatal screening for critical cardiovascular anomalies using pulse oximetry. *Arch Dis Child Fetal Neonatal Ed*, 0: 1-5.

Punukollu, M., Hamden, A., & Tulloh, R. (2011). Easily missed? Coarctation of the aorta in the newborn. *BMJ*, 343: 6838.

Reller, M. D., Strickland, M. J., Riehle-Colarusso, T., Mahle, W. T., & Correa, A. (2008). Prevalence of congenital heart defects in metropolitan Atlanta, 1998-2005. *J Pediatr*, 153(6): 807.

Richmond, S., & Wren, C. (2001). Early diagnosis of congenital heart disease. *Semin Neonatol*, 6: 27-35.

Rosenthal, E. (2005). Coarctation of the aorta from fetus to adult: curable condition or life long disease process? *Heart*, 91: 1495-1502.

Sinha, I. P., Mayell, S. J., & Halfhide, C. (2013). Pulse oximetry in Children. Arch Dis Child Educ Pract Ed: Published Online 4 Dec. 2013, doi: 10.1136/archdischild-2013-305526.

Thangaratinam, S., Brown, K., Zamora, J., Khan, K. S., Ewer, A. K. (2012). Accuracy of pulse oximetry in screening for congenital heart disease in asymptomatic newborns: a systematic review. *Lancet*, 92(3): 176-180.

Ward, K. E., Pryor, R. W., Matson, J. R., Razook, J. D., Thompson, W. M., & Elkins, R. C. (1990). Delayed Detection of Coarctation in Infancy: Implications for Timing of Newborn Follow-up. *Pediatrics*, 86: 972.

Wren, C., Renhardt, Z., Khawaja K. (2008). Twenty-year trends in diagnosis of life-threatening neonatal cardiovascular malformations. *Arch Dis Child Fetal Neonatal*, 93: 33-35.

What is claimed is:

1. A method for detecting an aortic coarctation in an infant comprising:

a) obtaining photoplethysmographic (PPG) signals from a right hand and from a foot of the infant using a photoplethysmograph of at least two channels;

b) selecting a section of the PPG signals without movement noise for analysis, low-pass filtering the PPG signals to reduce high frequency noise, and smoothing the PPG signals using a moving average filter;

c) identifying end-diastolic maxima and minima of systolic decrease for hand PPG pulses and for the foot PPG pulses from the PPG signals, and using the end-diastolic maxima and minima of systolic decrease to determine one or both of the following:
c1) time delay (TD) between the end-diastolic maxima for the hand PPG pulses and the end-diastolic maxima for the foot PPG pulses (f-hTD), and/or
c2) PPG pulse amplitude (AM) between the end-diastolic maxima and minima of systolic decrease for the hand PPG pulses and for the foot PPG pulses;
d) if PPG pulse amplitude (AM) is determined, determining a relative pulse amplitude (rAM) by dividing the AM by the minima of systolic decrease to obtain a rAM for the foot (rAM-F) PPG pulses and a rAM for the hand (rAM-H) PPG pulses;
e) calculating mean and standard deviation (SD) of f-hTD, and/or rAM for the foot (rAM-F) and rAM for the hand (rAM-H) for the PPG pulses in a selected section of PPG pulses, and discarding values deviating from the mean by 2 standard deviations or more from the calculation of the mean;
f) if mean foot rAM-F and mean hand rAM-H are calculated, determining a ratio F/H between mean foot rAM-F and mean hand rAM-H, and/or determining a ratio H/F between mean hand rAM-H and mean foot rAM-F; and optionally, obtaining a multiplication product of H/F times f-hTD and/or a multiplication product of F/H times f-hTD; and
g) detecting the aortic coarctation in the infant if one or more of:
the f-hTD is elevated above normal, or
the ratio F/H is decreased below normal, or
the ratio H/F is increased above normal, or
the product H/F times f-hTD is increased above normal.

2. The method of claim 1, wherein an aortic coarctation is determined using f-hTD.

3. The method of claim 1, wherein an aortic coarctation is determined using ratio F/H.

4. The method of claim 1, wherein an aortic coarctation is determined using f-hTD and ratio F/H.

5. The method of claim 1, wherein an aortic coarctation is determined using the product H/F times f-hTD.

6. The method of claim 1, wherein the f-hTD values for normal infants have a range of 15-50 milliseconds (ms) and a mean of 35 ms.

7. The method of claim 1, wherein the f-hTD value equal to or higher than a predetermined value in a range of 50-60 ms is indicative that the infant has an aortic coarctation.

8. The method of claim 1, wherein the f-hTD value of 50 ms or more is indicative that the infant has an aortic coarctation.

9. The method of claim 1, wherein the f-hTD value of 55 ms or more is indicative that the infant has an aortic coarctation.

10. The method of claim 1, wherein the f-hTD value of 60 ms or more is indicative that the infant has an aortic coarctation.

11. The method of claim 1, wherein infants without an aortic coarctation have a mean ratio F/H of 0.9.

12. The method of claim 1, wherein the ratio F/H equal to or less than a predetermined value in a range of 0.4-0.6 is indicative that the infant has an aortic coarctation.

13. The method of claim 1, wherein the ratio F/H of 0.6 or less is indicative that the infant has an aortic coarctation.

14. The method of claim 1, wherein the ratio F/H of 0.5 or less is indicative that the infant has an aortic coarctation.

15. The method of claim 1, wherein the ratio F/H of 0.4 or less is indicative that the infant has an aortic coarctation.

16. The method of claim 1, wherein infants without an aortic coarctation have a mean product of ratio H/F times f-hTD of 45.

17. The method of claim 1, wherein a product of ratio H/F times the f-hTD equal to or higher than a predetermined value in a range of 80-100 is indicative that the infant has an aortic coarctation.

18. The method of claim 1, wherein a product of ratio H/F times the f-hTD of 80 or more is indicative that the infant has an aortic coarctation.

19. The method of claim 1, wherein a product of ratio H/F times the f-hTD of 90 or more is indicative that the infant has an aortic coarctation.

20. The method of claim 1, wherein a product of ratio H/F times the f-hTD of 100 or more is indicative that the infant has an aortic coarctation.

21. The method of claim 1, wherein the f-hTD value equal to or higher than a predetermined value in a range of 50-60 ms and a ratio F/H equal to or less than a predetermined value in a range of 0.4-0.6 is indicative that the infant has an aortic coarctation.

22. A system for detecting an aortic coarctation in an infant comprising a photoplethysmograph of at least two channels, a computing device comprising a processor operably connected to the photoplethysmograph and a computer-readable storage medium operably connected to the processor, and a display device operably connected to the photoplethysmograph and to the processor, where the computer-readable storage medium includes computer-readable code that is read by the processor to perform a method comprising the steps of:
a) accessing photoplethysmographic (PPG) signals from a right hand and from a foot of the infant;
b) identifying end-diastolic maxima and minima of systolic decrease for hand PPG pulses and for foot PPG pulses from the PPG signals, and using the end-diastolic maxima and minima of systolic decrease to determine one or both of the following:
b1) time delay (TD) between the end-diastolic maxima for the hand PPG pulses and the end-diastolic maxima for the foot PPG pulses (f-hTD), and/or
b2) PPG pulse amplitude (AM) between the end-diastolic maxima and minima of systolic decrease for the hand PPG pulses and for the foot PPG pulses;
c) if PPG pulse amplitude (AM) is determined, determining a relative pulse amplitude (rAM) by dividing the AM by the minima of systolic decrease to obtain a rAM for the foot (rAM-F) PPG pulses and a rAM for the hand (rAM-H) PPG pulses;
d) calculating mean and standard deviation (SD) of f-hTD, and/or rAM for the foot (rAM-F) and rAM for the hand (rAM-H) for the PPG pulses in the selected section, and discarding values deviating from the mean by 2 standard deviations or more from the calculation of the mean;
e) if mean foot rAM-F and mean hand rAM-H are calculated, determining a ratio F/H between mean foot rAM-F and mean hand rAM-H, and/or determining a ratio H/F between mean hand rAM-H and mean foot rAM-F; and optionally, obtaining a multiplication product of H/F times f-hTD and/or a multiplication product of F/H times f-hTD; and
f) outputting to the display device one or more of f-hTD, ratio F/H, ratio H/F, f-hTD and ratio F/H, the product H/F times f-hTD, and the product F/H times f-hTD.

23. A method for treating an infant with an aortic coarctation, the method comprising
performing or having performed a method for detecting the aortic coarctation in an infant, and
treating the infant so identified with aortic coarctation using surgical intervention;
wherein the method for detecting the aortic coarctation in the infant comprises the steps of
a) obtaining photoplethysmographic (PPG) signals from a right hand and from a foot of the infant using a photoplethysmograph of at least two channels;
b) selecting a section of the PPG signals without movement noise for analysis, low-pass filtering the PPG signals to reduce high frequency noise, and smoothing the PPG signals using a moving average filter;
c) identifying end-diastolic maxima and minima of systolic decrease for hand PPG pulses and for foot PPG pulses from the PPG signals, and using the end-diastolic maxima and minima of systolic decrease to determine one or both of the following:
c1) time delay (TD) between the end-diastolic maxima for the hand PPG pulses and the end-diastolic maxima for the foot PPG pulses (f-hTD), and/or
c2) PPG pulse amplitude (AM) between the end-diastolic maxima and minima of systolic decrease for the hand PPG pulses and for the foot PPG pulses;
d) if PPG pulse amplitude (AM) is determined, determining a relative pulse amplitude (rAM) by dividing the AM by the minima of systolic decrease to obtain a rAM for the foot (rAM-F) PPG pulses and a rAM for the hand (rAM-H) PPG pulses;
e) calculating mean and standard deviation (SD) of f-hTD, and/or rAM for the foot (rAM-F) and rAM for the hand (rAM-H) for the PPG pulses in a selected section of PPG pulses, and discarding values deviating from the mean by 2 standard deviations or more from the calculation of the mean;
f) if mean foot rAM-F and mean hand rAM-H are calculated, determining a ratio F/H between mean foot rAM-F and mean hand rAM-H, and/or determining a ratio H/F between mean hand rAM-H and mean foot rAM-F, and optionally, obtaining a multiplication product of H/F times f-hTD and/or a multiplication product of F/H times f-hTD, and
g) detecting the aortic coarctation in the infant if one or more of:
the f-hTD is elevated above normal, or
the ratio F/H is decreased below normal, or
the ratio H/F is increased above normal, or
the product H/F times f-hTD is increased above normal.

* * * * *